United States Patent [19]
Lee

[11] Patent Number: 5,968,019
[45] Date of Patent: Oct. 19, 1999

[54] SAFETY SYRINGE

[75] Inventor: Rahnfong Lee, Taipei, Taiwan

[73] Assignee: Tun Huang International Development and Investment Co., Ltd., Taipei, Taiwan

[21] Appl. No.: 09/160,614

[22] Filed: Sep. 24, 1998

[30]  Foreign Application Priority Data

Jul. 14, 1998 [TW]  Taiwan .................................. 87211321

[51] Int. Cl.$^6$ ...................................................... A61M 5/00
[52] U.S. Cl. ........................................... 604/195; 604/110
[58] Field of Search .................................... 604/195, 198, 604/263, 218, 110, 187

[56]  References Cited

U.S. PATENT DOCUMENTS

| 5,256,151 | 10/1993 | Chul ......................................... | 604/195 |
| 5,336,186 | 8/1994 | Haber et al. ............................. | 604/110 |
| 5,489,272 | 2/1996 | Wirtz .................................. | 604/195 X |
| 5,634,903 | 6/1997 | Kurose et al. ........................... | 604/110 |

*Primary Examiner*—John D. Yasko
*Attorney, Agent, or Firm*—Thomas Schneck

[57]  ABSTRACT

A safety syringe includes an injection head, a plunger and a barrel. The injection head has a needle cannula mounted to a needle seat, with the needle seat attachable to a needle seat connector. The inner side of the rear end of the needle seat connector has stoppers that correspond to protrusions on the coupling portion of the plunger. The plunger has a plunger shaft connected by a conical section to a coupling portion that has a rubber gasket. The plunger shaft can be snapped off at the conical section after use, so as to completely disable the syringe. The safety syringe has a barrel for receiving the injection head portion and the plunger such that a liquid-tight chamber is formed to hold medicine or blood. The injection head is attached to the barrel through interlocking annular edges and grooves, and remains so attached during the withdrawal of fluid and during the injection phase. After the injection, the user simply rotates the plunger shaft, engages the stoppers of the needle seat connector with the protrusions of the plunger, and pulls the injection head into the barrel of the syringe with the plunger. Once extracted, the plunger is broken off at the conical section, thereby protecting the needle cannula and preventing reuse.

5 Claims, 6 Drawing Sheets

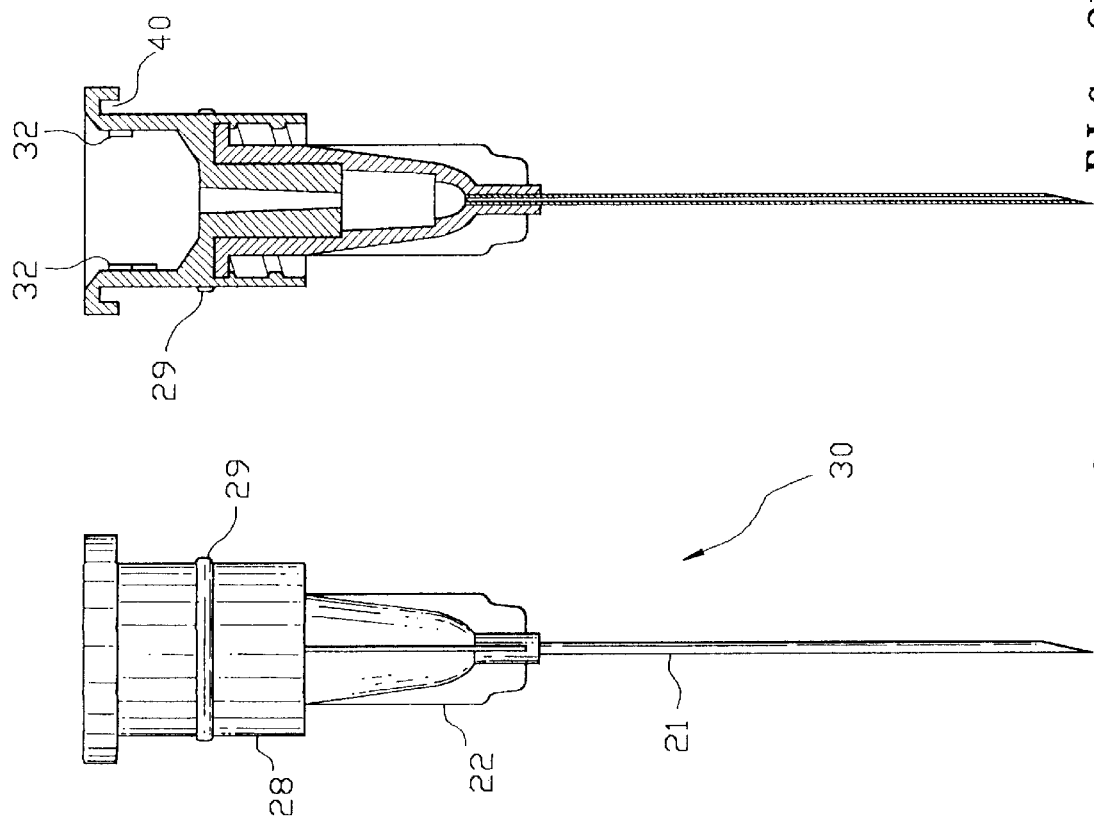

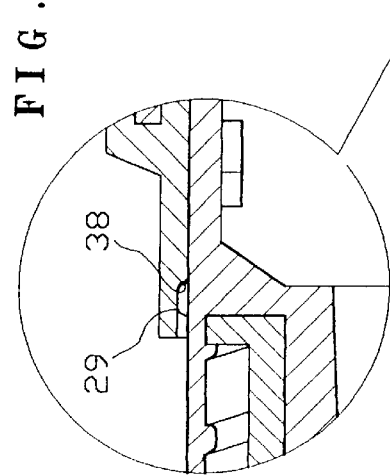
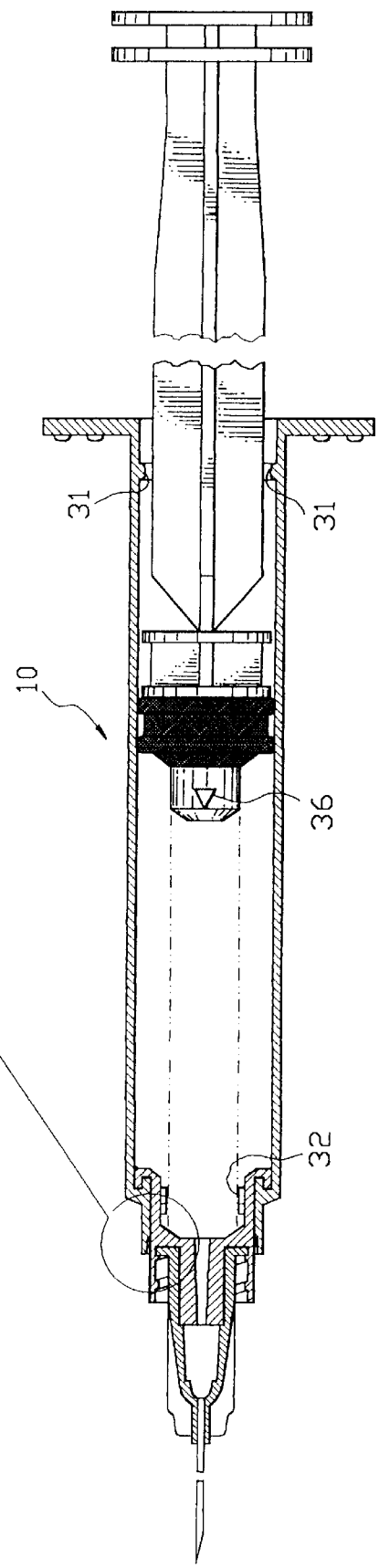

SAFETY SYRINGE

FIELD OF THE INVENTION

The present invention relates to a syringe, and more particularly, to a safety syringe, which can retract a used needle cannula into a barrel to prevent the needle tip from puncturing the user's fingers.

DESCRIPTION OF THE PRIOR ART

For a long time, a serious problem has existed in the use of syringes. Clinical personnel are often punctured by the used needle cannula of a syringe, thereby contracting hepatitis, AIDS, etc. Hence, clinical personnel are always taught to be careful when using syringes so as to avoid being punctured by the used needle cannula of a syringe. A better solution, however, is to develop a new safety syringe that eliminates this problem.

The inventor of the present invention has invented several syringe structures, such as the syringes disclosed in R.O.C. (Taiwan) Utility Model Publication No. 165,304 entitled "Safety Syringe Structure", No. 252,346 entitled "Safety Syringe Structure (Patent-of-addition 1)", and No. 320,056 entitled "Safety Syringe Structure (Patent-of-addition 2)", as well as U.S. Pat. No. 5,344,403 entitled "Simple Retractable Safety Syringe."

Although the syringes under the aforesaid four patents are all safe to use, there are still some disadvantages. For example, it is not easy for the plunger to pull the injection head portion and the needle cannula into the barrel. Also, the amount of residual dosage remaining in the syringe, which cannot be injected into a patient's body, is significant. It is also difficult for the injection head portion to be pushed into position and ready to withdraw the medicine for injection into the patient's body. When using the plunger to push the injection head portion into the barrel, the plunger cannot push the injection head portion into position if the applied force is too small, yet if the force is too great the plunger and the injection head portion will be irrevocably engaged due to the connection method employed.

Hence, the development of an easier to use and safer syringe is an important issue.

OBJECT OF THE INVENTION

It is therefore an object of the present invention to provide a safety syringe having a simple structure, which is easy to manufacture and use, and can prevent the user from being punctured.

It is another object of the present invention to provide a safety syringe, which can easily retract the injection head portion together with the needle cannula into the barrel, and also can easily push the injection head portion into position.

A further object of the present invention is to provide a safety syringe which can effectively decrease the residual dosage.

SUMMARY OF THE INVENTION

The safety syringe according to the present invention comprises an injection head portion, a plunger, and a barrel. A coupling portion is formed at the front end of the plunger head, and can be inserted into a space at the inner side of the rear end of the needle seat connector. The side surface of the coupling portion has a plurality of protrusions. The inner side surface of the needle seat connector of the injection head portion has a plurality of stoppers corresponding to the protrusions of the plunger head. When an injection action in completed, the plunger will abut against the inner edge of the front end opening of the barrel such that the coupling portion of the plunger head can be inserted into the space at the inner side of the rear end of the needle seat connector. By rotating the plunger shaft, the protrusions of the coupling portion will be engaged with the corresponding stoppers and by pulling in the plunger back toward the rear end of the barrel, the injection head portion, which is now connected with the plunger head, can be retracted into the barrel.

BRIEF DESCRIPTION OF THE DRAWINGS

These and other attributes of the present invention will become more clear upon a thorough study of the following description of the preferred embodiment for carrying out the invention, particularly when reviewed in conjunction with the drawings, wherein:

FIG. 2A is a side view of an injection head portion of the safety syringe in accordance with the present invention;

FIG. 2B is a sectional view of an injection head portion of the safety syringe in accordance with the present invention;

FIG. 2C is an end view of an injection head portion of the safety syringe in accordance with the present invention;

FIG. 2D is a perspective view of an injection head portion of the safety syringe in accordance with the present invention;

FIG. 4A is a schematic view showing the plunger of the safety syringe of the present invention in a moving condition, in which the sections of the barrel and injection head portion are shown;

FIG. 4B is a partial enlarged sectional view showing the first flange of the needle seat connector abutting against the beveling portion at the inner side of the front end of the barrel;

DETAILED DESCRIPTION OF THE INVENTION

Please refer to FIGS. 1–7.

Figure 1:
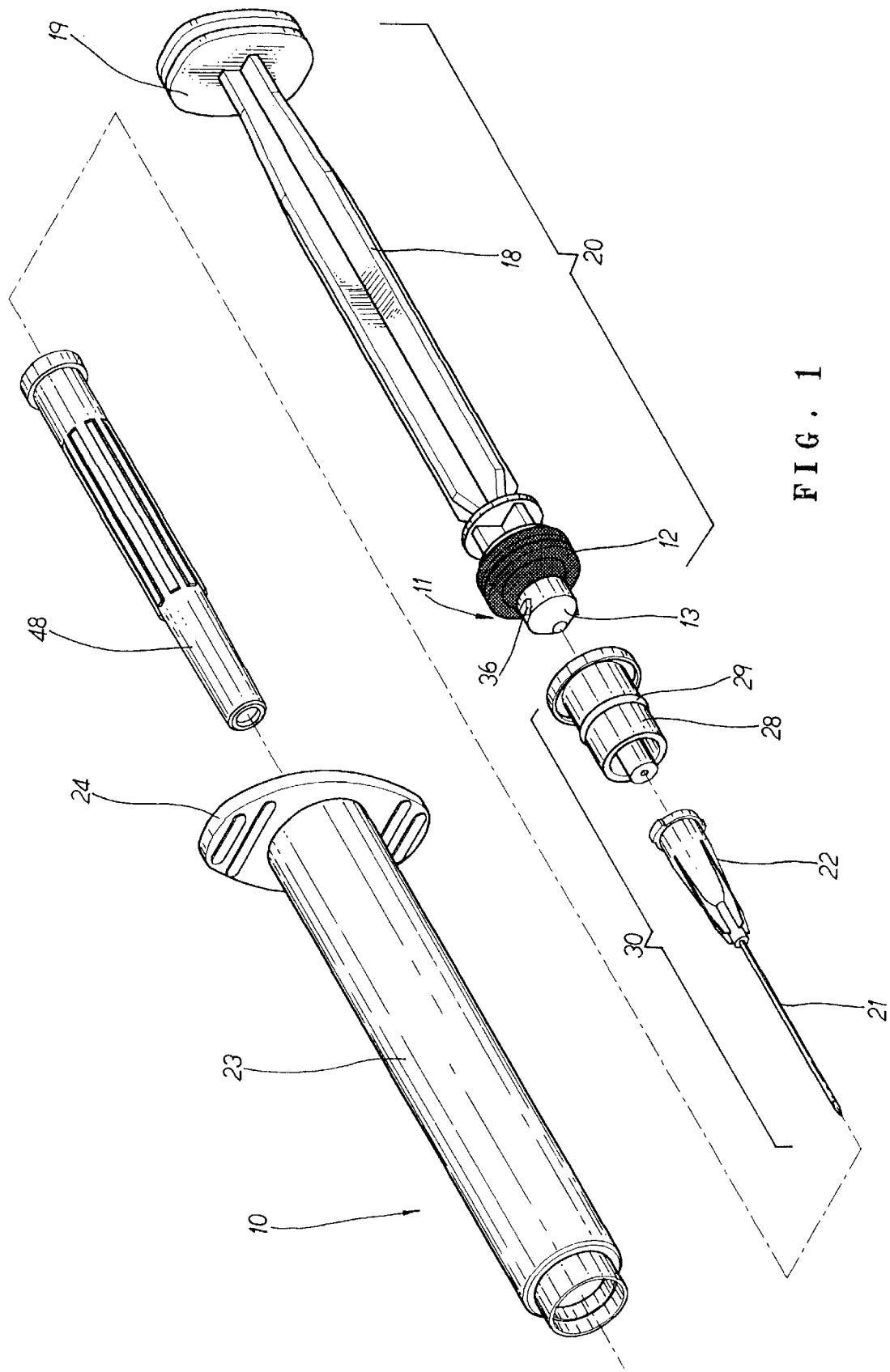
FIG. 1 is an exploded perspective view of a safety syringe in accordance with the present invention.
Figure 3B:
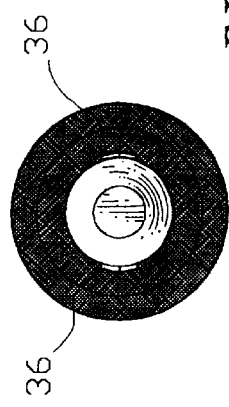
FIG. 3B is an end view of a plunger of the safety syringe in accordance with the present invention.
Figure 3A:
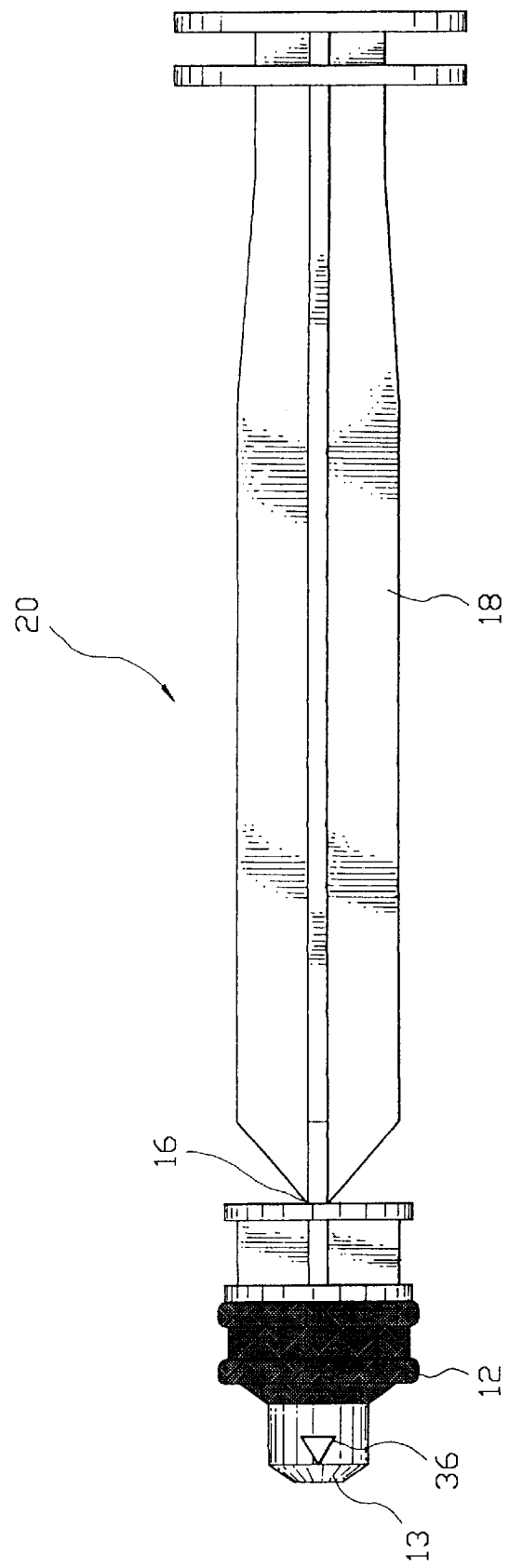
FIG. 3A is a side view of a plunger of the safety syringe in accordance with the present invention.
Figure 5:
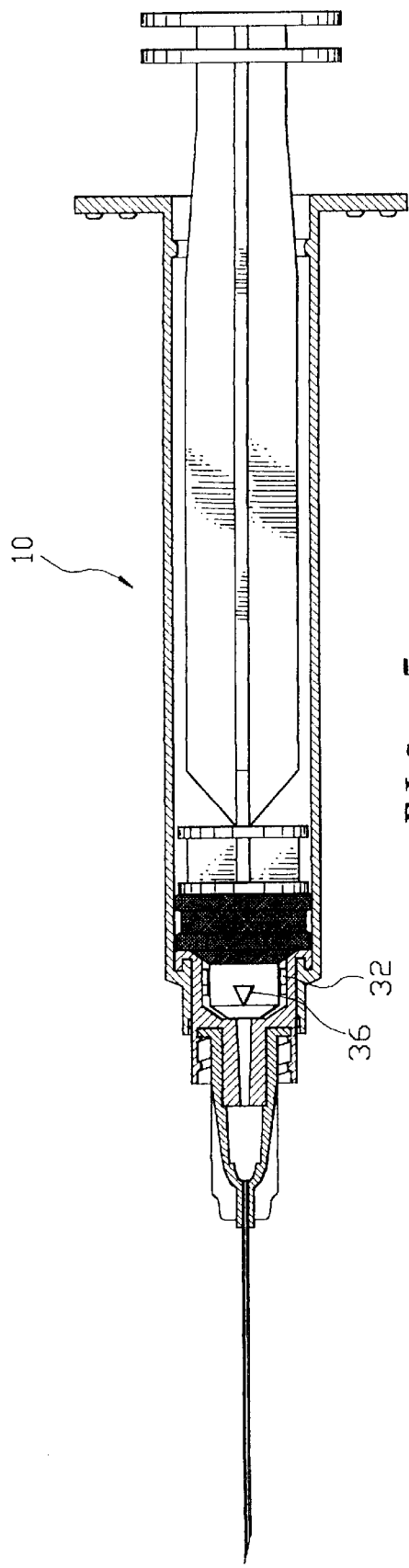
FIG. 5 is a schematic view showing the plunger of the safety syringe of the present invention abutting against the injection head portion, in which the sections of the barrel and the injection head portion are shown.
Figure 6:
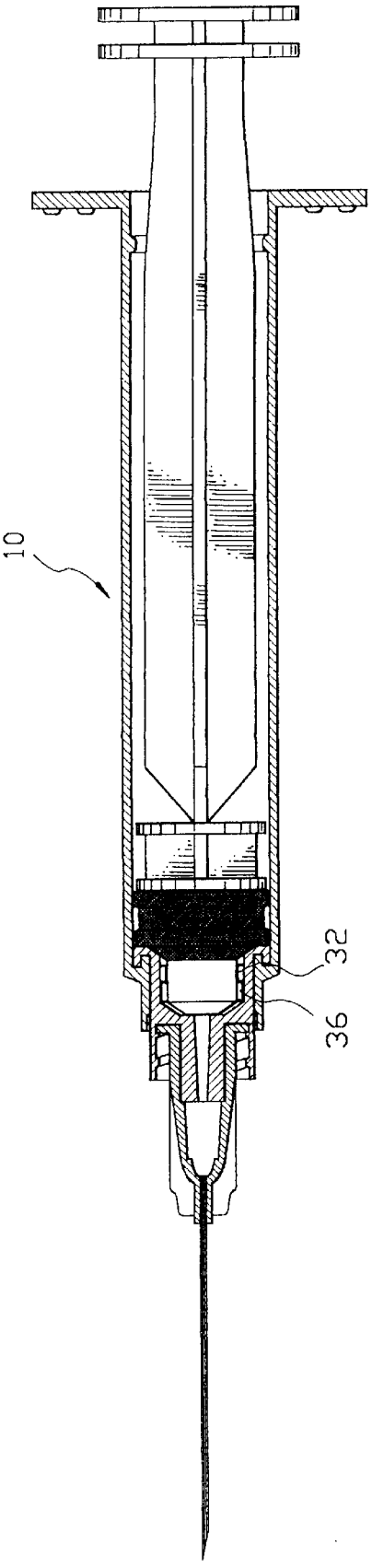
FIG. 6 is a schematic view showing the plunger of FIG. 5 being rotated at an angle of 90.
Figure 7:
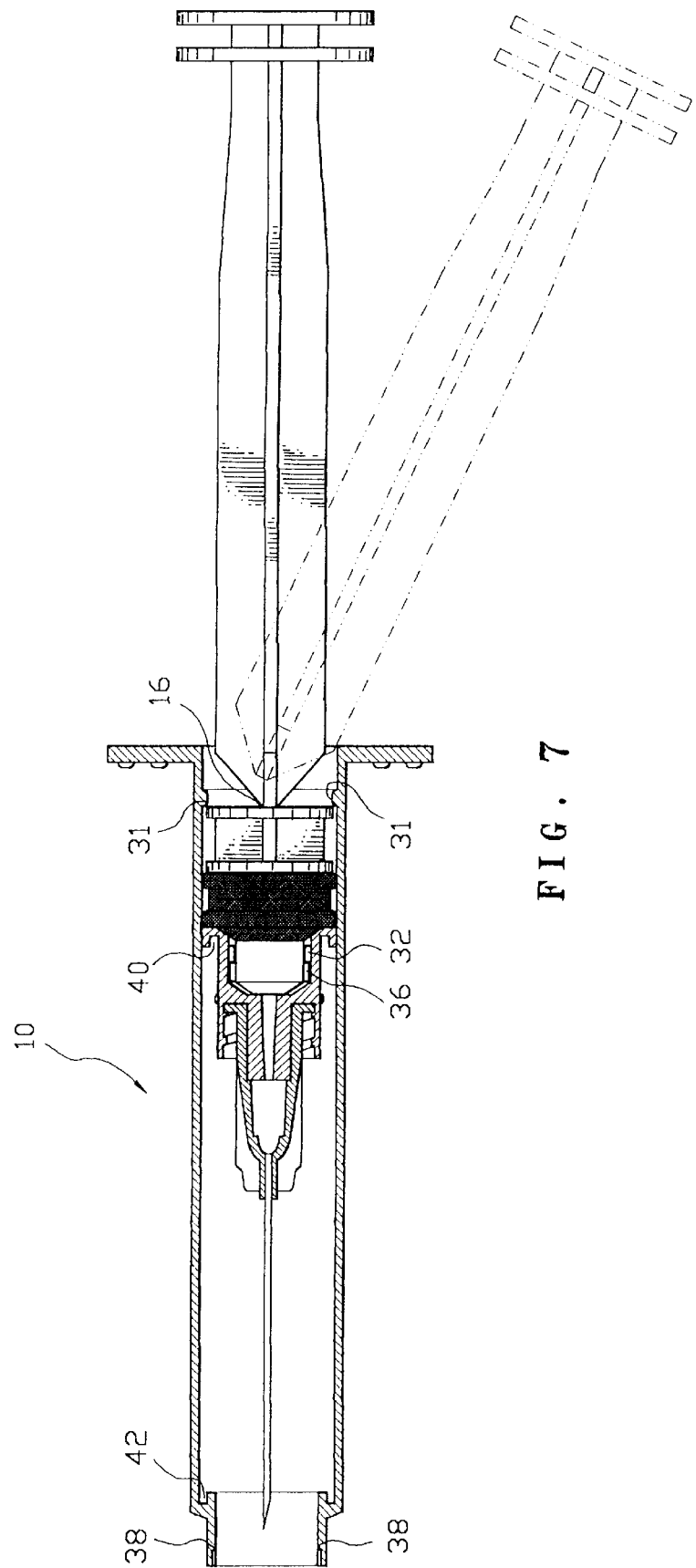
FIG. 7 is a schematic view showing the plunger of the safety syringe of the present invention pulling the injection head portion together with the needle cannula into the barrel, and the plunger shaft being broken, in which the sections of the barrel and injection head portion are shown.

The safety syringe 10 of the present invention includes an injection head portion 30 having an injection needle cannula 21, a needle seat 22 fixed onto the bottom of the needle cannula 21, and a needle seat connector 28 for mounting the needle seat 22 (see FIGS. 1, 2A and 2B); a plunger 20 having a plunger shaft 18, a rubber ring 12 and a plunger head 11 (see FIGS. 1 and 3A); and a barrel 23 for receiving the injection head portion 30 and the plunger 20 such that the injection head portion 30 can extend beyond a front end opening, and the plunger 20 can extend beyond a rear end opening of the barrel 23 and move into the injection head portion 30 (see FIGS. 1, 4A and 5). A beveling portion 38 is provided at the inner side of the front end of the barrel 23 in order to abut against a first flange 29 of the needle seat connector 28 to obtain a tight engagement (see FIGS. 1, 2A, 2B, 2D, 4A, 4B, 5–7). The inner side of the rear end of the barrel 23 is provided with a second flange 31 for blocking the plunger 20 (see FIGS. 4A and 7).

A significant improvement of the present invention resides in that a coupling portion 13 is formed at the front end of the plunger head 11, and can be inserted into a space at the inner side of the rear end of the needle seat connector 28. The side surface of the coupling portion 13 has a plurality of protrusions 36 (see FIGS. 1, 3A, 3B, 4A and 5–7), and the inner side surface of the needle seat connector 28 of the injection head portion 30 has a plurality of stoppers 32 corresponding to the protrusions 36 of the plunger head 11 (see FIGS. 2B–2D, 4A, and 5–7). When an injection action is completed, the plunger 20 will abut against the inner edge of the front end opening of the barrel 23 such that the coupling portion 13 of the plunger head 11 can be inserted into the space at the inner side of the rear end of the needle seat connector 28 (see FIG. 5). By rotating the plunger shaft 18, the protrusions 36 of the coupling portion 13 will be engaged with the corresponding stoppers 32 (see FIG. 6), and by pulling the plunger 20 back toward the rear end of the barrel 23, the injection head portion 30, which is now connected with the plunger head 11, can be retracted into the barrel (see FIG. 7).

The safety syringe has several other attributes that contribute to the safety of the apparatus. A conical section 16, which can be easily broken off, can also be formed between the plunger head 11 and the plunger shaft 18. After the injection head portion 30 is retracted into the barrel 23 by means of the plunger 20, the plunger shaft 18 protruding from the barrel 23 can be removed by breaking the conical section 16 (see FIGS. 1, 3A and 7). Furthermore the shapes of the stoppers 32 may vary. It is preferable that at least one of the stoppers 32 is provided with a recess 34 (see FIG. 2D) that can be engaged with the protrusion 36 in order to prevent the re-rotating of the plunger 20 after the protrusions 36 are engaged with the stoppers 32 (see FIG. 2D). Also, an annular outer edge 40 of an L-shaped section is formed at the rear end of the needle seat connector 28, and an annular groove 42 corresponding to the annular outer edge 40 is formed at the inner side of the front end of the barrel 23 such that the annular outer edge 40 can be inserted into the annular groove 42 from the inside of the barrel 23 in order to connect the injection head portion 30 with the barrel 23 (see FIGS. 2B, 4A, 5–7). Finally, for increased safety, the syringe 10 can further comprise a tip protector 48 to cover the injection head portion 30 (see FIG. 1).

A finger flange 24 can be provided near the opening at the rear end of the barrel 23, and a thumb rest 19 can be provided at the rear end of the plunger shaft 18; as can be seen in conventional syringes. However, in order to facilitate the application of enough force to rotate the plunger shaft 18, the thumb rest 19 is preferably a double-layer structure having an elliptical shape (see FIGS. 1, 3A, 4A and 5–7).

The present invention is not limited by the forgoing description of the embodiments, and may be embodied in other specific forms without departing from the spirit or essential characteristic of the appended claims.

What is claimed is:

1. A safety syringe comprising:

an injection head portion, having an injection needle cannula, a needle seat fixed onto the bottom of the needle cannula, a needle seat connector for attaching the needle seat, with said needle seat connector having an annular outer edge formed at the rear end for affixing the needle seat connector to a barrel;

a plunger, having a plunger shaft, a rubber ring and a plunger head;

a barrel for receiving the injection head portion and the plunger such that the injection head portion can extend beyond a front end opening, and the plunger can extend beyond a rear end opening of the barrel and move into the injection head portion; a beveling portion at the inner side of the front end of the barrel abutting against a first flange of the needle seat connector obtaining a tight engagement; an annular groove defined in the inner side of the front end of the barrel, forming a liquid-tight seal with the annular outer edge of the needle seat connector; the inner side of the rear end of the barrel having a second flange for blocking the plunger;

a coupling portion formed at the front end of the plunger head, for insertion into a space at the inner side of the rear end of the needle seat connector; the side surface of the coupling portion having a plurality of protrusions;

wherein the inner side surface of the needle seat connector of the injection head portion has a plurality of stoppers corresponding to the protrusions of the plunger head; and whereby when an injection action is completed, the plunger will abut against the inner edge of the front end opening of the barrel such that the coupling portion of the plunger head can be inserted into the space at the inner side of the rear end of the needle seat connector; by rotating the plunger shaft, the protrusions of the coupling portion will be engaged with the corresponding stoppers; by pulling the plunger back toward the rear end of the barrel, the injection head portion, which is now connected with the plunger head, can be retracted into the barrel.

2. A safety syringe as claimed in claim 1, wherein at least one of said plurality of stoppers is provided with a recess that can be irreversibly engaged with at least one of said plurality of protrusions in order to prevent the uncoupling of the plunger after the protrusions are engaged with the stoppers.

3. A safety syringe as claimed in claim 1, wherein a conical section, which can be easily broken off, can also be formed between the plunger head and the plunger shaft; after the injection head portion is retracted into the barrel by means of the plunger, the plunger shaft protruding from the barrel can be removed by breaking the conical section.

4. A safety syringe as claimed in claim 1, wherein an annular outer edge of an L-shaped section is formed at the rear end of the needle seat connector, and an annular groove corresponding to the annular outer edge is formed at the inner side of the front end of the barrel such that the annular outer edge can be inserted into the annular groove from the inside of the barrel in order to connect the injection head portion with the barrel.

5. A safety syringe as claimed in claim 1, wherein said syringe can further comprise a tip protector to cover the injection head portion.

* * * * *